United States Patent
Ohashi

(10) Patent No.: US 7,729,732 B2
(45) Date of Patent: Jun. 1, 2010

(54) BIOLOGICAL INFORMATION MEASURING APPARATUS AND METHOD FOR CONTROLLING THE APPARATUS

(75) Inventor: Mitsuo Ohashi, Yokohama (JP)

(73) Assignee: Spectratech Inc. (JP)

( * ) Notice: Subject to any disclaimer, the term of this patent is extended or adjusted under 35 U.S.C. 154(b) by 1136 days.

(21) Appl. No.: 11/351,348

(22) Filed: Feb. 9, 2006

(65) Prior Publication Data

US 2006/0222224 A1 Oct. 5, 2006

(30) Foreign Application Priority Data

Feb. 9, 2005 (JP) .............................. 2005-032942

(51) Int. Cl.
*A61B 5/1455* (2006.01)
(52) U.S. Cl. ...................... 600/310; 600/340
(58) Field of Classification Search .......... 600/309–344
See application file for complete search history.

(56) References Cited

U.S. PATENT DOCUMENTS

| | | | | |
|---|---|---|---|---|
| 5,553,614 | A * | 9/1996 | Chance | 600/407 |
| 6,240,309 | B1 * | 5/2001 | Yamashita et al. | 600/473 |
| 6,505,133 | B1 * | 1/2003 | Hanna et al. | 702/74 |
| 6,850,314 | B2 * | 2/2005 | Le | 356/5.11 |
| 7,194,292 | B2 * | 3/2007 | Norris | 600/323 |

FOREIGN PATENT DOCUMENTS

| | | |
|---|---|---|
| JP | 2000-172407 A | 6/2000 |
| JP | 2002-248104 A | 9/2002 |
| JP | 2003-207443 A | 7/2003 |
| JP | 2004-248849 A | 9/2004 |
| JP | 2004-333344 A | 11/2004 |

* cited by examiner

*Primary Examiner*—Eric F Winakur
(74) *Attorney, Agent, or Firm*—Rossi, Kimms & McDowell LLP

(57) ABSTRACT

A biological information measuring apparatus includes a plurality of light emission sections, a plurality of light detection sections, and a control section. Each light emission section injects, into a living organism, a spectrum-modulated light beam having a specific wavelength. The control section acquires a spread code sequence employed by each of the light emission sections for spread spectrum modulation, and supplies the spread code sequence to the light detection sections. By use of the spread code sequence, each light detection section selectively receives a specific reflected light beam having the spread code sequence, which is selected from among the light beams which have been emitted from the light emission sections and reflected in the living organism. Subsequently, each light detection section despreads an electrical signal corresponding to the thus-received reflected light beam, and outputs a detection signal corresponding to the intensity of the reflected light beam.

11 Claims, 7 Drawing Sheets

BIOLOGICAL INFORMATION MEASURING APPARATUS AND METHOD FOR CONTROLLING THE APPARATUS

BACKGROUND OF THE INVENTION

1. Field of the Invention

The present invention relates to a biological information measuring apparatus for acquiring various types of biological information associated with the metabolism of a living organism, such as biological density, water content, blood oxygen level, glucose level, blood glucose level, and pulse, on the basis of the mechanism that the transmission of light through a living organism necessary signal with wavelength of the light; and to a method for controlling the apparatus.

2. Background Art

In recent years, there have been actively proposed, as an apparatus and method for conveniently analyzing the interior of a living organism in a noninvasive manner, apparatuses and methods for acquiring information on the interior of a living organism by emitting light from a light source provided on the surface of the living organism to the interior of the organism, and receiving reflected light which has been transmitted through the living organism while being scattered and absorbed therein, and which has reached the living organism surface. For example, Japanese Patent Application Laid-Open (kokai) No. 2000-172407 discloses a biological optical measuring apparatus including, as main components, a semiconductor laser, a modulator, an optical fiber, a photodetector, and a multi-channel lock-in amplifier. Particularly, this biological optical measuring apparatus can acquire information on, for example, cerebral activity at the cerebral cortical layer through measurement of blood oxygen saturation on the basis of a change in absorption of near-infrared light by hemoglobin.

In the apparatus disclosed in Japanese Patent Application Laid-Open (kokai) No. 2000-172407, the multi-channel lock-in amplifier selectively detects beams of light which reach the photodetector. However, this apparatus may fail to eliminate adverse effects on measurement caused by, for example, mutual interference (crosstalk) between light beams emitted from the semiconductor laser, or outside light (e.g., light from an inverter-type fluorescent lamp), leading to limited measurement accuracy.

Japanese Patent Application Laid-Open (kokai) No. 2003-207443 discloses an optical measuring apparatus including at least one of a plurality of amplification means and a plurality of attenuation means, the amplification means respectively amplifying signals measured at light-receiving sections, and the attenuation means respectively attenuating the intensities of light beams entering the light-receiving sections. This optical measuring apparatus can maintain the intensity of necessary signals at an optimal level by varying the amplification factor of the amplification means or the attenuation factor of the attenuation means in accordance with the light emitting/receiving conditions, which change during the course of measurement. Meanwhile, Japanese Patent Application Laid-Open (kokai) No. 2004-248849 discloses a multi-channel optical measuring apparatus in which the arrangement of light-emitting points and light-receiving points is optimized in a probe, whereby a light-receiving point receives light emitted from a specific light-emitting point. In this multi-channel optical measuring apparatus, light-emitting points and light-receiving points are arranged so as to form a pattern of equilateral triangles, whereby the distance between a light-emitting point and a light-receiving point is optimized, and at the light-receiving point, light emitted from the specific light-emitting point is received.

However, in the optical measuring apparatus disclosed in Japanese Patent Application Laid-Open (kokai) No. 2003-207443 or the multi-channel optical measuring apparatus disclosed in Japanese Patent Application Laid-Open (kokai) No. 2004-248849, a necessary light beam is selectively received merely by varying the intensity of light emitted from a light-emitting point as measured at the corresponding light-receiving point. Therefore, a light beam to be received (necessary light beam) is not actively identified, and thus adverse effects of light crosstalk or outside light on measurement may fail to be avoided.

In order to solve the above-described problems, the present applicant has proposed a biological information measuring apparatus and a measurement method employing the apparatus, which are disclosed in Japanese Patent Application Laid-Open (kokai) No. 2002-248104. Specifically, this biological information measuring apparatus includes a light emission section which emits light which has undergone spread spectrum modulation by use of a pseudo-noise sequence; and a light detection section which receives the spread-spectrum-modulated light, and outputs a detection signal obtained through despreading of the above-modulated signal. The biological information measuring apparatus and measurement method can eliminate light beams which do not have the same pseudo-noise sequence, and thus can actively avoid adverse effects of light crosstalk or outside light on measurement.

In the case where multi-channel measurement is to be performed by means of the biological information measuring apparatus described in Japanese Patent Application Laid-Open (kokai) No. 2002-248104, in which the light detection section identifies light beams having two wavelengths emitted from the light emission section, a number of combination units, each including the light emission section and the light detection section, must be arranged. Therefore, the apparatus may become large in size, and multi-channel measurement may become physically difficult. Recently, particularly, demand has arisen for an apparatus which enables measurement of biological information with improved accuracy, and real-time observation of detailed measurement results.

SUMMARY OF THE INVENTION

The present invention has been accomplished in order to solve the aforementioned problems. An object of the present invention is to provide a biological information measuring apparatus which enables noninvasive, detailed measurement of biological information associated with the metabolism of a living organism. Another object of the present invention is to provide a method for controlling the apparatus.

The present invention provides a biological information measuring apparatus comprising a plurality of light emission means, each adapted for modulating a predetermined primary modulated signal by spread spectrum modulation to thereby generate a secondary modulated signal, and for injecting a light beam into a living organism on the basis of the secondary modulated signal; light detection means for receiving the light beams which have been emitted from the plurality of light emission means and transmitted through the living organism, for obtaining an electrical signal corresponding to the light beams through despreading, and for detecting a signal contained in the light beams on the basis of the electrical signal; and control means for controlling the operation of the light emission means and the light detection means, and for obtaining biological information associated with the metabolism of the living organism on the basis of the signal detected by the light detection means. A characteristic feature of the biological information measuring apparatus resides in that the control means comprises spread code sequence acquisition means for acquiring, from specific light emission means selected from among the plurality of light emission means, a spread code sequence employed by the specific light emission means for spread spectrum modulation of the predetermined primary modulated signal; and spread code sequence supply means for supplying, to the light detection means, the spread code sequence acquired by the spread code sequence acquisition means. Preferably, the light emission means and the light detection means are arranged in, for example, the form of a matrix. Preferably, the light emission means and the light detection means are connected to the living organism via light conducting means (e.g., an optical fiber).

In the biological information measuring apparatus, preferably, the plurality of light emission means comprise a plurality of light generation means for respectively generating light beams having different specific wavelengths, and each of the light generation means comprises spread code sequence generation means for generating the aforementioned spread code sequence; spread spectrum modulation means for generating the secondary modulated signal through spread spectrum modulation of the predetermined primary modulated signal supplied from the control means by use of the above-generated spread code sequence; and light source driving means for driving a light source which emits a light beam having a specific wavelength on the basis of the secondary modulated signal generated by the spread spectrum modulation means. Preferably, the spread code sequence generation means comprises periodic random number acquisition means for acquiring periodic random numbers supplied from the control means, and a frequency synthesizer for generating a random pattern regarding frequency in accordance with the above-acquired periodic random numbers. Preferably, the spread code sequence generation means generates the spread code sequence by varying a chip frequency represented by the inverse number of the duration of occurrence of the spread code sequence. Preferably, the light beams having different specific wavelengths which are respectively generated by the plurality of light generation means enter the aforementioned living organism while being superposed on one another.

Preferably, the light detection means comprises light receiving means for receiving the light beams which have been transmitted through the living organism and for generating an electrical signal corresponding to the received light; spread code sequence acquisition means for acquiring a spread code sequence supplied from the control means; despreading means for despreading the electrical signal by use of the thus-acquired spread code sequence so as to demodulate a signal contained in the light beams transmitted through the living organism; and output means for outputting the thus-demodulated signal to the control means.

The present invention also provides a method for controlling a biological information measuring apparatus comprising a plurality of light emission means, each adapted for modulating a predetermined primary modulated signal by spread spectrum modulation to thereby generate a secondary modulated signal, and for injecting a light beam into a living organism on the basis of the secondary modulated signal; light detection means for receiving the light beams which have been emitted from the plurality of light emission means and transmitted through the living organism, for obtaining an electrical signal corresponding to the light beams through despreading, and for detecting a signal contained in the light beams on the basis of the electrical signal; and control means for controlling the operation of the light emission means and the light detection means, and for obtaining biological information associated with the metabolism of the living organism on the basis of the signal detected by the light detection means. A characteristic feature of the method resides in that the method comprises controlling the control means to select specific light emission means from among the plurality of light emission means, to acquire a spread code sequence employed by the thus-selected specific light emission means for spread spectrum modulation of the predetermined primary modulated signal, and to supply the thus-acquired spread code sequence to the light detection means.

In the method, when biological information is measured in a depth direction of the living organism, preferably, the control means selects, as specific light emission means from among the plurality of light emission means, light emission means whose distance from the light detection means becomes equal to one of various distances. Preferably, the control means generates, with respect to the specific light emission means, the spread code sequence employed by the specific light emission means for spread spectrum modulation of the predetermined primary modulated signal by varying a chip frequency represented by the inverse number of the duration of occurrence of the spread code sequence.

According to the present invention, the plurality of light emission means can respectively inject a plurality of spectrum modulated light beams having different specific wavelengths into a living organism. The light detection means employs the spread code sequences employed by the light emission means, and thus the light detection means can selectively receive the light beams which have been emitted from the specific light emission means and transmitted through the living organism, can despread an electrical signal corresponding to the light beams, and can detect a signal contained in the light beams. Therefore, even when a number of light emission means are provided, the light detection means can actively avoid adverse effects of light crosstalk or outside light. Since one light detection means can identify and receive light beams emitted from the plurality of light emission means, the number of the light detection means required for measurement can be reduced, and the apparatus per se can be downsized.

Also, the light detection means can selectively detect light beams having different specific wavelengths emitted from specific light emission means, and can output, for each of the light beams having different specific wavelengths, a signal including information obtained when the light beams are transmitted through the living organism. Therefore, points at which biological information is measured can be densely arranged; i.e., the measurement resolution can be improved considerably, and the control means can measure biological information more accurately and in more detail.

When biological information is measured in a depth direction of a living organism, the control means can cause the light detection means to identify specific light emission means such that the distance between the light detection means and the light emission means varies. Specifically, when biological information is measured at a shallow point, the control means can cause the light detection means to identify specific light emission means such that the distance between the light detection means and the light emission means is shortened, whereas when biological information is measured at a deep point, the control means can cause the light detection means to identify specific light emission means such that the distance between the light detection means and the light emission means is lengthened. Therefore, biological information can be measured at points of different depths in a living organism; i.e., biological information can be measured in a three-dimensional manner. On the basis of the three-dimensionally measured biological information, the interior of the living organism can be observed in a three-dimensional and detailed manner.

Since a spread code sequence can be generated by varying the chip frequency, a rapid biological change in a living organism (e.g., nervous activity in a living organism) can also be measured as biological information. Specifically, when a spread code sequence is generated by significantly varying a chip frequency, the bandwidth of light which is emitted from the light emission means on the basis of a spread-spectrum-modulated signal can be increased. When biological information is measured by use of the light of increased bandwidth, a change in the light scattering state associated with such a rapid biological change can be detected. Therefore, when the chip frequency is appropriately varied in accordance with the rate of change in biological information to be measured, the biological information can be measured in a very accurate and detailed manner. In addition, a rapid change occurring in a living organism can be real-time observed by displaying a signal output from the light detection means on, for example, a display apparatus.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with the accompanying drawings, in which.

DETAILED DESCRIPTION OF PREFERRED EMBODIMENTS

Figure 1:
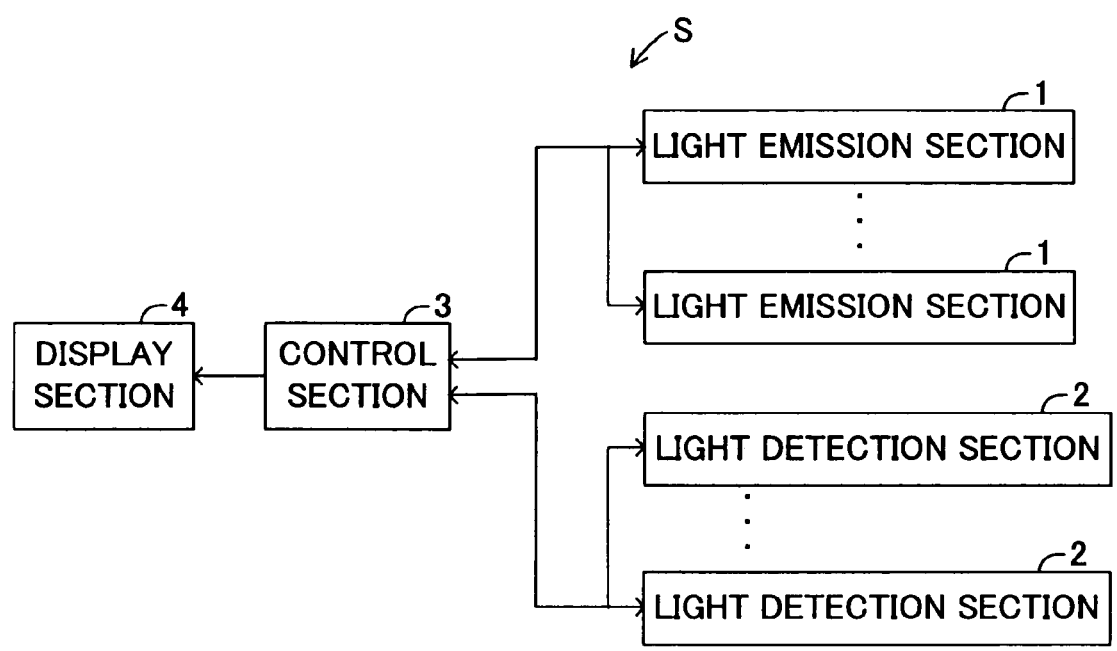
FIG. 1 is a block diagram schematically showing a biological information measuring apparatus according to an embodiment of the present invention.

An embodiment of the present invention will next be described with reference to the drawings. FIG. 1 is a block diagram schematically showing the configuration of a biological information measuring apparatus S according to the present invention. As shown in FIG. 1, the biological information measuring apparatus S includes a plurality of light emission sections 1 which emit light beams having specific wavelengths; and a plurality of light detection sections 2 which detect the light beams which have been emitted from the light emission sections 1 and transmitted through a living organism.

The light emission sections 1 and the light detection sections 2 are connected to a control section 3. The control section 3 includes, as a main component, a microcomputer including CPU, ROM, RAM, a timer, etc., and totally controls the operation of the biological information measuring apparatus S. The control section 3 calculates biological information (e.g., blood oxygen level in the brain) on the basis of the intensities of light beams detected by the light detection sections 2; more specifically, the intensities of light beams emitted from the light emission sections 1, which have been attenuated through propagation through a living organism. The control section 3 outputs data representing the thus-calculated biological information to a display section 4. The display section 4 is formed of, for example, a liquid crystal display, and displays the biological information in a predetermined mode on the basis of the data supplied from the control section 3.

Figure 2:
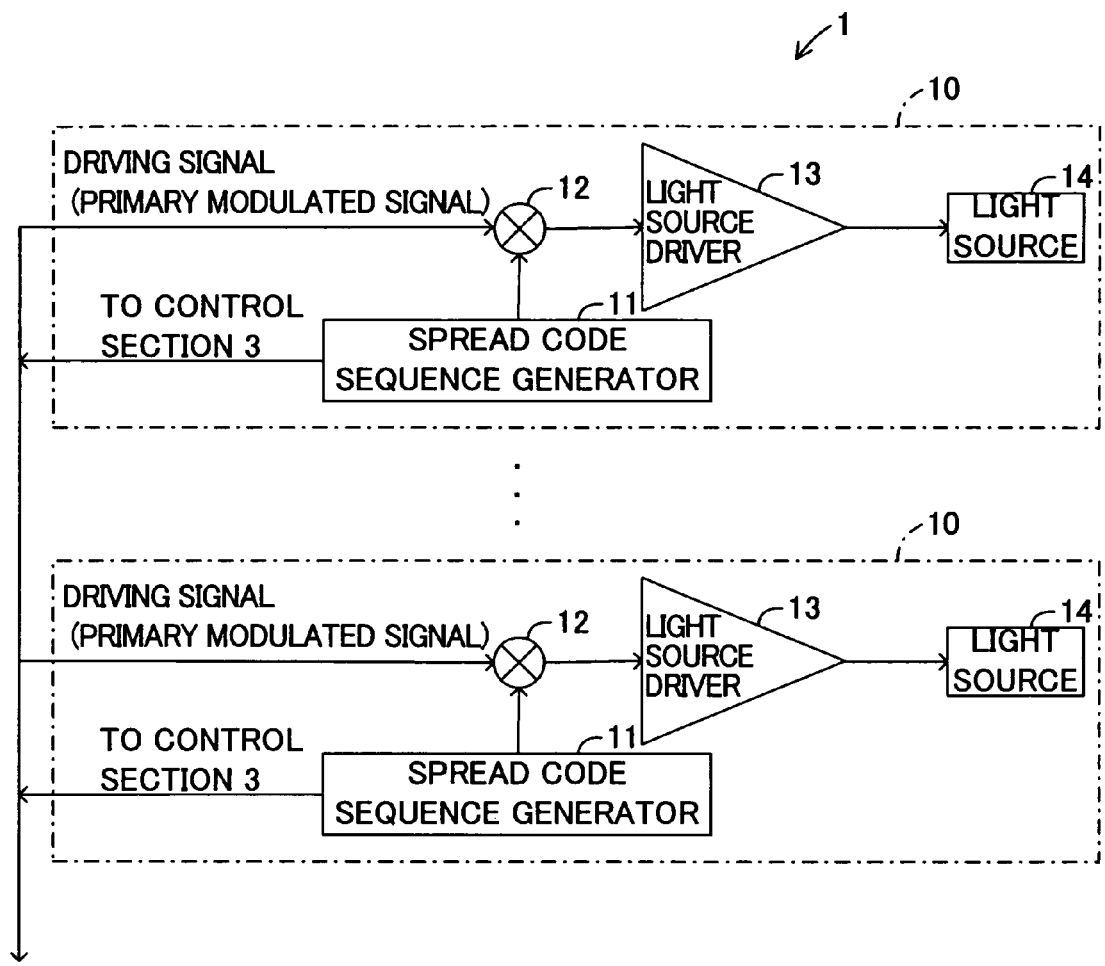
FIG. 2 is a block diagram schematically showing the configuration of a light emission section shown in FIG. 1.

The light emission sections 1 will next be described in detail. As shown in a block diagram of FIG. 2, each of the light emission sections 1 is formed of a plurality of light generation units 10 which generate light beams having different specific wavelengths. In the present embodiment, the light emission section 1 is formed of six light generation units 10. Each of the light generation units 10 emits a light beam having a specific wavelength on the basis of a spread-spectrum-modulated signal. Therefore, each of the light generation units 10 includes a spread code sequence generator 11 for generating a spread code sequence such as a 128-bit pseudorandom noise (PN) sequence which consists of "+1" and "−1." The spread code sequence generator 11 generates, for example, a Hadamard sequence, an M sequence, or a Gold code sequence as a PN sequence.

The aforementioned Hadamard sequence, M sequence, and Gold code sequence are similar to those employed for spread spectrum modulation, and thus detailed description of their generation methods is omitted. However, these sequences will next be described briefly. The Hadamard sequence is obtained from each of the rows or columns of a Hadamard matrix which consists of "+1" and "−1." The M sequence is a binary sequence obtained by use of a shift register consisting of n 1-bit register units, each memorizing "0" or "+1." The shift register is configured such that the exclusive logical sum of the value of an intermediate register unit and the value of the final register unit is fed to the first register unit. Notably, in order to transform this binary sequence into a PN sequence, the value "0" is converted into "−1" through level conversion. The Gold code sequence is basically obtained through addition of two types of M sequences. Therefore, the Gold code sequence can increase the number of sequences considerably, as compared with the case of the M sequence. Among these sequences serving as PN sequences, two arbitrary sequences are orthogonal with each other, and the sum of products of the two sequences yields the value "0." That is, one of these sequences has zero correlation with the other sequences.

The PN sequence generated by the spread code sequence generator 11 is output to the control section 3, and is also output to a multiplier 12. The multiplier 12 multiplies a driving signal (primary modulated signal) supplied from the control section 3 by the PN sequence supplied from the spread code sequence generator 11. Thus, the driving signal (primary modulated signal) can be subjected to spread spectrum modulation. The multiplier 12 supplies the thus-spread-spectrum-modulated driving signal (i.e., secondary modulated signal) to a light source driver 13. The multiplier 12 serves as the spread spectrum modulation means of the apparatus of the present invention.

The light source driver 13 drives a light source 14 on the basis of the secondary modulated signal. The light source 14 is appropriately selected from among, for example, a semiconductor laser, a light-emitting diode, a solid-state laser, and a gas laser. The light source 14 generates a spread-spectrum-modulated light beam having a specific wavelength falling within a range of 600 to 1,000 nm (hereinafter the light beam may be referred to as a "modulated light beam"). In the present embodiment, as described above, the light emission section 1 is formed of six light generation units 10. In this case, the light source 14 of each of the light generation units 10 generates a modulated light beam having a wavelength of, for example, 695, 730, 780, 805, 830, or 950 nm. In the present embodiment, the light emission section 1, which is formed of the six light generation units 10, emits modulated light beams having six specific wavelengths. However, no particular limitation is imposed on the number of the light generation units 10, which constitute the light emission section 1; i.e., the number of the specific wavelengths of modulated light beams emitted from the section 1. Needless to say, the number of the specific wavelengths of modulated light beams emitted from the section 1 may be, for example, 2 to 3, or 7 or more.

Figure 3:
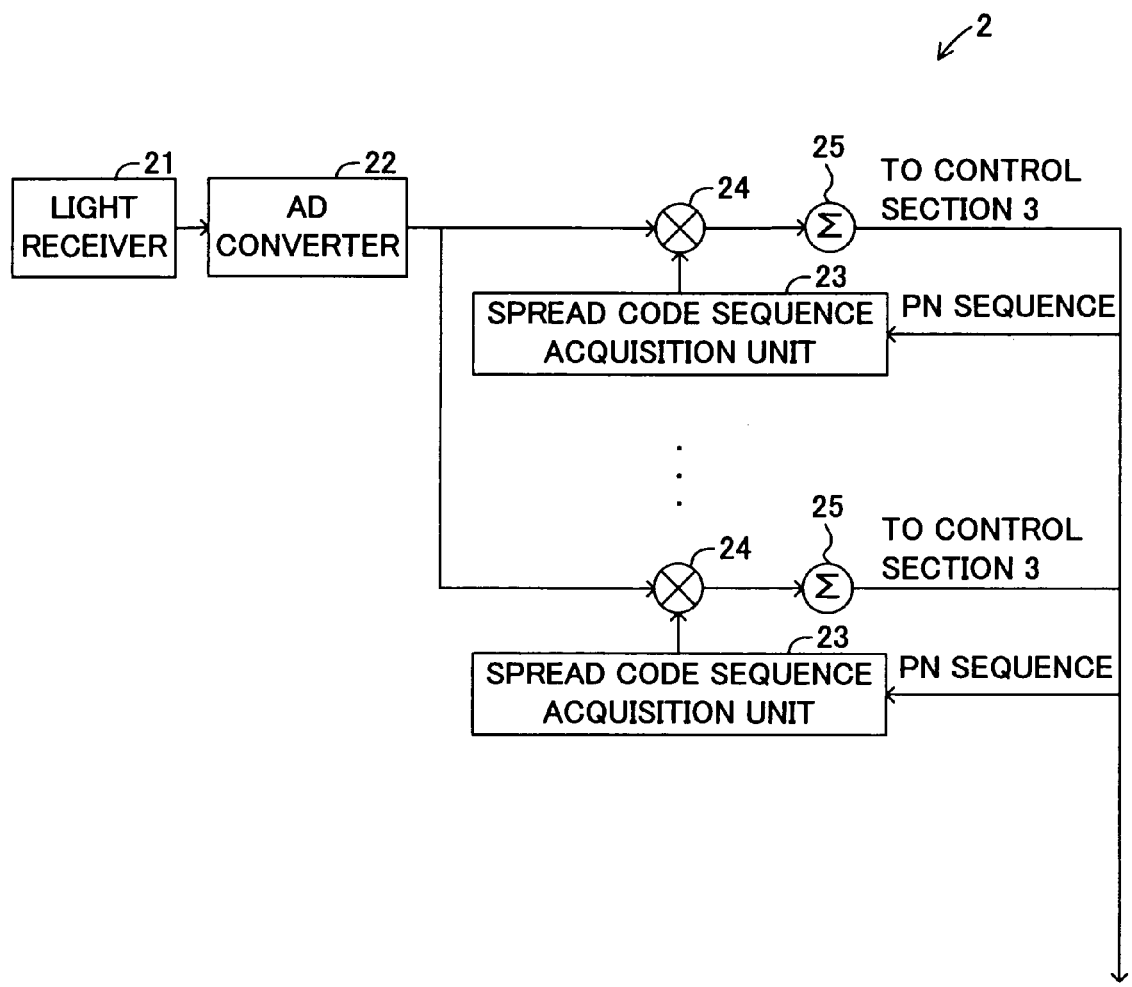
FIG. 3 is a block diagram schematically showing the configuration of a light detection section shown in FIG. 1.

As shown in a block diagram of FIG. 3, each of the light detection sections 2 includes a light receiver 21. The light receiver 21 includes, for example, a photodiode as a main component. The light receiver 21 receives modulated light beams which have been emitted from the light sources 14 of the light emission section 1 and transmitted through a living organism, and outputs an electrical detection signal to an AD converter 22 in a time-series manner. The AD converter 22 converts the electrical detection signal (analog signal) output from the light receiver 21 into a digital signal, and outputs the digital signal to multipliers 24.

The light detection section 2 includes a plurality of spread code sequence acquisition units 23 for selectively receiving modulated light beams from a specific light emission section 1 among the plurality of light emission sections 1 provided around the section 2. A spread code sequence acquisition unit 23 acquires, from the control section 3, the spread code sequence (i.e., PN sequence) contained in the modulated light beams emitted from the specific light emission section 1. The spread code sequence acquisition unit 23 supplies the thus-acquired PN sequence to the corresponding multiplier 24.

The multiplier 24 multiplies the detection signal output from the AD converter 22 by the PN sequence supplied from the spread code sequence acquisition unit 23. Subsequently, the multiplier 24 outputs the thus-calculated product of the detection signal and the PN sequence to an accumulator 25. The accumulator 25 accumulates the thus-supplied product over one or more periods of the above-supplied PN sequence. Subsequently, the accumulator 25 outputs, to the control section 3, a detection signal corresponding to the modulated light beams which have been emitted from the specific light emission section 1 and attenuated in the living organism. The multiplier 24 and the accumulator 25 serve as the despreading means of the apparatus of the present invention, and the accumulator 25 serves as the output means of the apparatus of the present invention.

Figure 4:
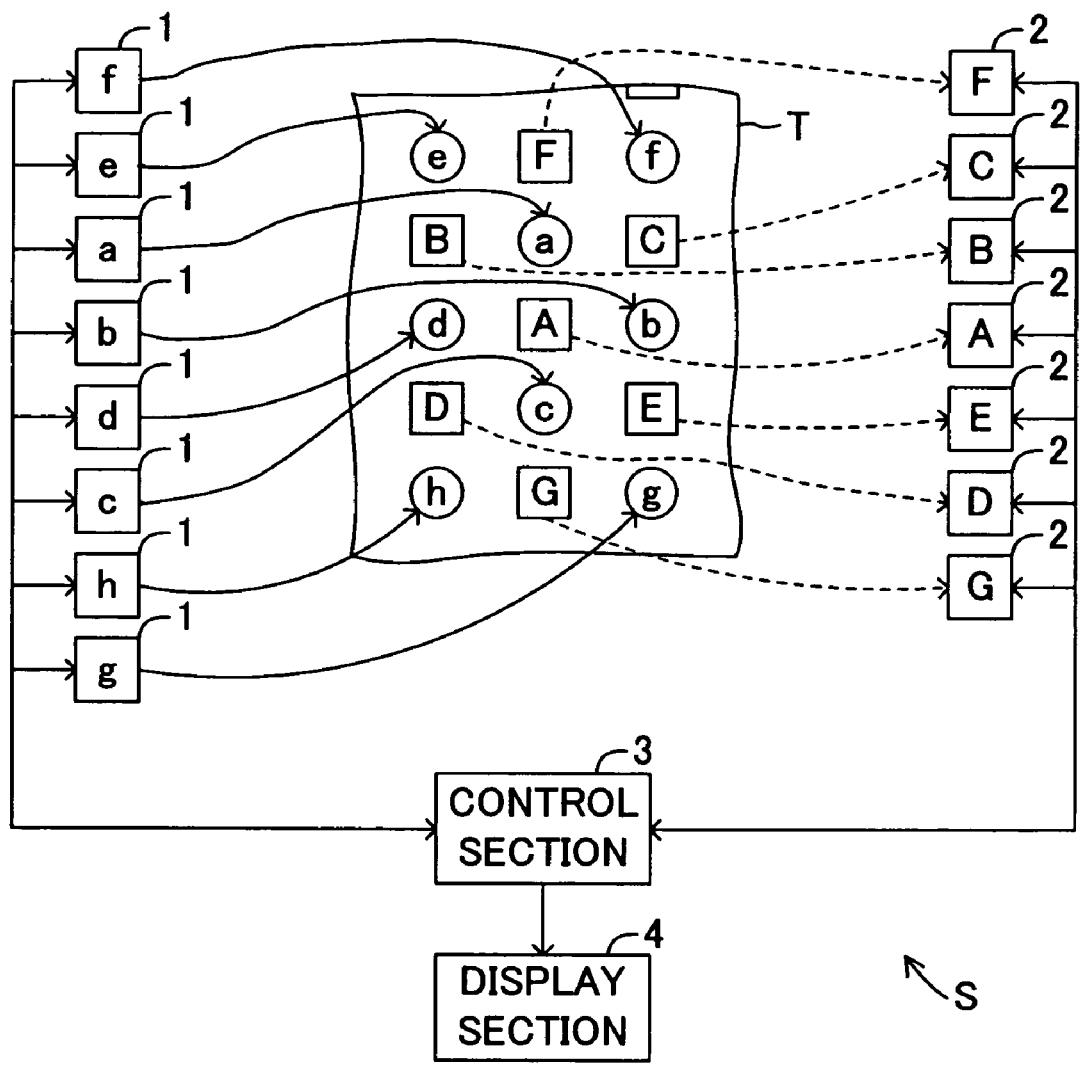
FIG. 4 shows a part of the arrangement of incident points and light-receiving points in the case where the biological information measuring apparatus of FIG. 1 is applied to measurement of blood oxygen level in the brain.

The biological information measuring apparatus S, which has the above-described configuration, will now be described by taking, as an example, the case where the blood oxygen level in the brain (i.e., biological information) is measured through operational control of the control section 3. When the blood oxygen level in the brain is measured, as shown in FIG. 4, modulated light beams emitted from the light emission sections 1 are supplied to circular points a to h (hereinafter may be referred to as "incident points a to h") on the surface of a head T. The light detection sections 2 detect the modulated light beams (hereinafter may be referred to as "reflected light beams") which have been transmitted through the head T and have reached square points A to G (hereinafter may be referred to as "light-receiving points A to G"). The incident points a to h and the light-receiving points A to G are arranged in the form of a matrix. In the following description of operation, the light emission sections 1 which emit modulated light beams to the incident points a to h will be respectively called "light emission sections a to h," and the light detection sections 2 which detect reflected light beams which have reached the light-receiving points A to G will be respectively called "light detection sections A to G."

FIG. 4 shows only a part of the biological information measuring apparatus S. Therefore, the number of the incident points and the light-receiving points (i.e., the number of channels) is not limited to the number shown in FIG. 4, and the blood oxygen level in the brain can be measured by use of a greater number of incident points and light-receiving points which are arranged in the form of a matrix. When the distance between the head T and the light emission sections a to h and the distance between the head T and the light detection sections A to G are small, the blood oxygen level can be measured by bringing the light emission sections a to h and the light detection sections A to G into direct contact with the incident points a to h or the light-receiving points A to G, respectively. In contrast, when the distance between the head T and the light emission sections a to h and the distance between the head T and the light detection sections A to G are large, the blood oxygen level in the brain can be measured by connecting the light emission sections a to h with the incident points a to h by use of, for example, optical fibers, and connecting the light detection sections A to G with the light-receiving points A to G by use of, for example, optical fibers.

Emission of light beams by the light emission sections a to h will now be described. An operator operates a non-illustrated input apparatus, and gives an instruction to the control section 3 for designating a specific wavelength of modulated light beams to be injected into the head T. In this case, the operator can give an instruction to the control section 3 for specifying a plurality of specific wavelengths of modulated light beams to be emitted. According to this instruction, the control section 3 supplies driving signals to the light emission sections a to h for generating modulated light beams having the above-designated specific wavelengths. In the light emission sections a to h, on the basis of the thus-supplied driving signals, the light generation units 10 initiate their operations for generating modulated light beams having the above-designated specific wavelength.

Specifically, in each of the light generation units 10 of the light emission sections a to h, the spread code sequence generator 11 generates, for example, a Gold code sequence as a PN sequence. Subsequently, the spread code sequence generator 11 outputs the thus-generated PN sequence to the control section 3, as well as to the multiplier 12. The multiplier 12 calculates the product of the PN sequence and the driving signal supplied from the control section 3 (i.e., primary modulated signal), thereby subjecting the driving signal to spread spectrum modulation.

When the thus-spread-spectrum-modulated driving signal (i.e., secondary modulated signal) is supplied to the light source drivers 13, the light sources 14 (e.g., semiconductor lasers) of the light emission sections a to h emit modulated light beams having the specific wavelength to the incident points a to h. The modulated light beams injected through the incident points a to h pass through the skull of the head T, enter the cerebral cortical layer, and propagate through the cerebral cortical layer while being diffusely reflected (i.e., being attenuated). Subsequently, the modulated light beams again pass through the skull of the head T, and reach the surface of the head T. When a plurality of specific wavelengths are designated by the operator, each of the light emission sections a to h emits modulated light beams having six specific wavelengths such that the beams are superposed on one another. In this case, the modulated light beams emitted from the six light sources 14 of each of the light emission sections a to h are converged by means of, for example, an optical lens or a light collector which collects light beams conducting through optical fibers.

Detection of reflected light beams by the light detection sections A to. G will next be described. The modulated light beams which have reached the surface of the head T are detected as reflected light beams by the light detection sections A to G via the light-receiving points A to G. In this case, the modulated light beams injected through the incident points a to h reach the light-receiving points A to G as reflected light beams. For example, light beams which reach the light-receiving point A, as reflected light beams, include not only the modulated light beams injected through the incident points a, b, c, and d, which are located around the light-receiving point A, but also the modulated light beams injected through the incident points e, f, g, and h. Under this circumstance, the control section 3 controls the light detection section A such that the section A selectively receives, among all the reflected light beams that have reached the light-receiving point A, for example, reflected light beams corresponding to the modulated light beams injected through the incident points a, b, c, and d. Operation of the control section 3 for the above control will next be described specifically.

As described above, the control section 3 supplies the driving signals to the light emission sections a to h, and then acquires PN sequences from the light generation units 10. Subsequently, the control section 3 supplies, to the light detection section A, the PN sequences acquired from the spread code sequence generators 11 of the light emission sections a, b, c, and d. Thus, the spread code sequence acquisition units 23 of the light detection section A acquire the PN sequences contained in the modulated light beams emitted from the light emission sections a, b, c, and d, and supply the thus-acquired PN sequences to the multipliers 24.

In the light detection section A, the light receiver 21 receives all the reflected light beams that have reached the light-receiving point A, and outputs, to the AD converter 22, electrical detection signals corresponding to the thus-received reflected light beams in a time-series manner. The AD converter 22 converts the thus-output electrical detection signals into digital signals, and outputs the thus-digitized detection signals to the multipliers 24.

Each of the multipliers 24 calculates the product of the detection signal output from the AD converter 22 and the PN sequence supplied from the corresponding spread code sequence acquisition unit 23. Subsequently, the multiplier 24 outputs the thus-calculated product to the corresponding accumulator 25, and the accumulator 25 accumulates the thus-output product over one period (i.e., 128 bit length) or more of the PN sequence. Thus, through the processing for obtaining the sum of products performed by the multipliers 24 and the accumulators 25, the digitized detection signals can be correlated with the above-supplied PN sequences, whereby only detection signals corresponding to the modulated light beams from the light emission sections a, b, c, and d can be selected and output.

As described above, two different PN sequences are orthogonal with each other; i.e., the product of the different PN sequences becomes "0." Therefore, when, for example, a spread code sequence acquisition unit 23 supplies the PN sequence of the light emission section a to the corresponding multiplier 24, the product of the PN sequence of the light emission section a and a detection signal (among the detection signals output from the AD converter 22) other than the detection signal corresponding to the modulated light beam emitted from the light emission section a becomes "0." Therefore, the value obtained through accumulation by the accumulator 25 over at least one period of the PN sequence becomes "0," and the correlation becomes "0." Thus, a detection signal which does not have the PN sequence supplied from the spread code sequence acquisition unit 23 (or a detection signal which does not match the PN sequence); i.e., the reflected light beam of the modulated light beam emitted from any of the light emission sections b to h is selectively eliminated, and only the detection signal corresponding to the reflected light beam of the modulated light beam emitted from the light emission section a is output to the control section 3. Similarly, when the corresponding spread code sequence acquisition units 23 supply the PN sequences of the light emission sections b, c, and d, only the detection signals corresponding to the reflected light beams of the modulated light beams emitted from the light emission sections b, c, and d are output to the control section 3.

Thus, the light detection section A selectively detects, among the modulated light beams having the specific wavelengths emitted from the light emission sections a to h, the reflected light beams of the modulated light beams emitted from the light emission sections a to d, and the section A outputs, to the control section 3, the detection signals corresponding to the thus-detected reflected light beams. Similar to the case of the light detection section A, the light detection sections B to G are controlled by the control section 3. Therefore, the reflected light beams of the modulated light beams emitted from specific light emission sections of the light emission sections a to h can be selectively detected, and the detection signals corresponding to the thus-detected reflected light beams can be output.

When other specific wavelengths (total six specific wavelengths in the present embodiment) of modulated light beams to be injected into the head T are designated by the operator, the control section 3 repeatedly performs operational control in a manner similar to the aforementioned operational control, for modulated light beams having the thus-designated specific wavelengths, respectively. Thus, each of the light detection sections A to G can output, to the control section 3, the detection signals corresponding to the reflected light beams emitted from specific light emission sections among the reflected light beams of the modulated light beams having the other specific wavelengths emitted from the light emission sections a to h. When each of the light emission sections a to h emits modulated light beams having six specific wavelengths such that the beams are superposed on one another, the control section 3 outputs, to each of the spread code sequence acquisition units 23 of the light detection sections A to G, the PN sequence acquired from each of the spread code sequence generators 11 of the light emission sections a to h. Thus, the light detection sections A to G separate the reflected light beams of the superposed modulated light beams from one another, and output detection signals corresponding to the thus-separated reflected light beams.

When the detection signals are output from the light detection sections A to G, the control section 3 calculates the blood oxygen level in the brain (i.e., subject) on the basis of the thus-output detection signals, and outputs the thus-calculated blood oxygen level to the display section 4. The display section 4 displays the blood oxygen level in the brain in a predetermined mode. Detailed description of the method for calculating the blood oxygen level is omitted, since the calculation method is not related directly to the present invention. However, the blood oxygen level calculation method will next be described briefly.

Figure 5:
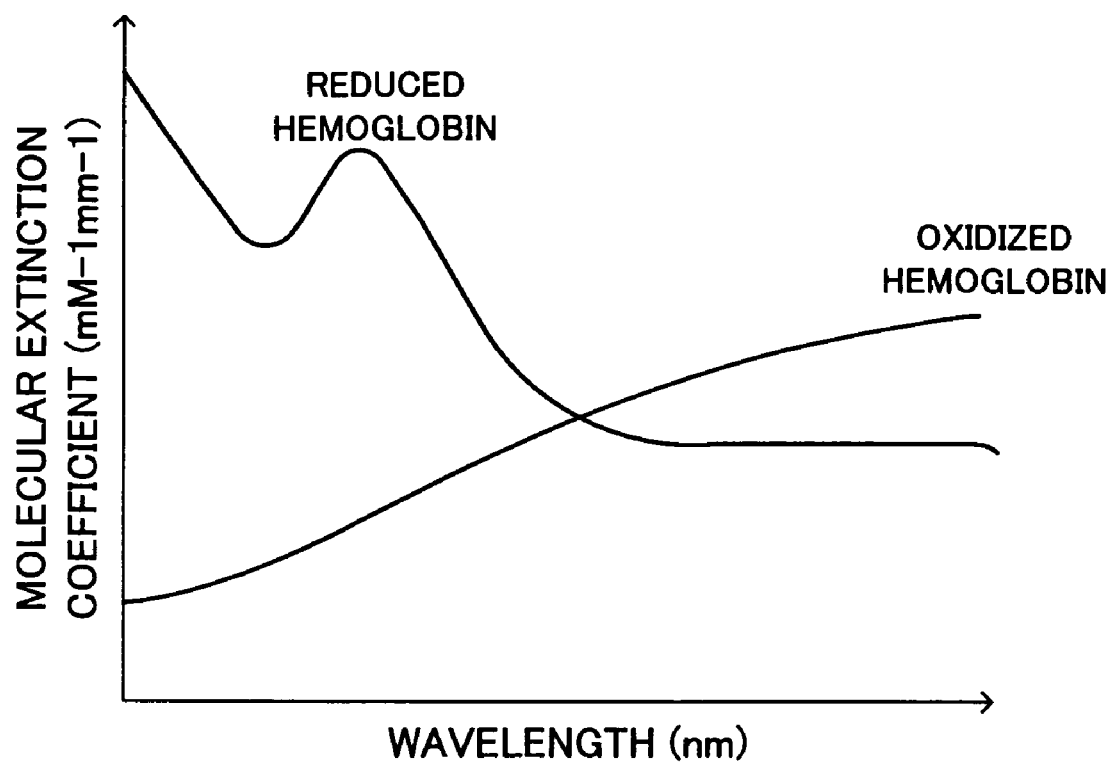
FIG. 5 is a graph schematically showing change in the molecular extinction coefficient of oxidized hemoglobin or reduced hemoglobin with respect to wavelength.

In the present embodiment, according to the Lambert-Beer law representing the relation between concentration and light attenuation, the blood oxygen level is calculated on the basis of the attenuation of modulated light beams caused by the difference in blood hemoglobin levels; i.e., the degree of absorption of the modulated light beams by hemoglobin. Hemoglobin in blood, which binds to oxygen and flows through blood vessels, plays a role in supplying oxygen to cells. Therefore, in blood flowing through arteries, the level of hemoglobin bound to oxygen (hereinafter may be referred to as "oxidized hemoglobin") is high, whereas in blood flowing veins, the level of hemoglobin not bound to oxygen (hereinafter may be referred to as "reduced hemoglobin") is high. As schematically shown in FIG. 5, each of oxidized hemoglobin and reduced hemoglobin which are present in blood exhibits an optical absorption spectrum in which the molecular extinction coefficient nonlinearly varies with respect to the wavelengths of emitted light beams (modulated light beams). The blood oxygen level in arteries or veins can be calculated according to the optical absorption spectra of oxidized hemoglobin and reduced hemoglobin; i.e., the Lambert-Beer law employing the molecular extinction coefficient, the intensities of emitted light beams (modulated light beams), and the intensities of light beams reflected by oxidized hemoglobin or reduced hemoglobin.

In the biological information measuring apparatus S according to the present embodiment, which operates as described above, each of the light emission sections a to h emits modulated light beams having six specific wavelengths to the head T (i.e., subject). Each of the light detection sections A to G detects the reflected light beams of the modulated light beams having the six specific wavelengths emitted from the specific light emission sections a to h, and outputs detection signals corresponding to the intensities of the thus-detected reflected light beams. According to the Lambert-Beer law, the control section 3 can calculate the blood oxygen level in arteries or veins (particularly in capillary vessels) more accurately and in more detail by use of the molecular extinction coefficients corresponding to the six specific wavelengths, the emission intensities of the modulated light beams having the six specific wavelengths, and the intensities of the reflected light beams having the six specific wavelengths represented by the detection signals output from the light detection sections A to G. In addition, when a specific wavelength (e.g., 695 nm or 730 nm) falling within a range in which the molecular extinction coefficient significantly varies in a nonlinear manner (see FIG. 5) is designated by the operator, the light emission sections a to h emit a modulated light beam having the thus-designated specific wavelength. Therefore, even in the case where modulated light beams have wavelengths falling within a range in which the molecular extinction coefficient varies in a nonlinear manner, when the detection signals output from the light detection sections A to G are employed, change in the blood oxygen level in arteries or veins can be accurately detected.

Figure 6A:
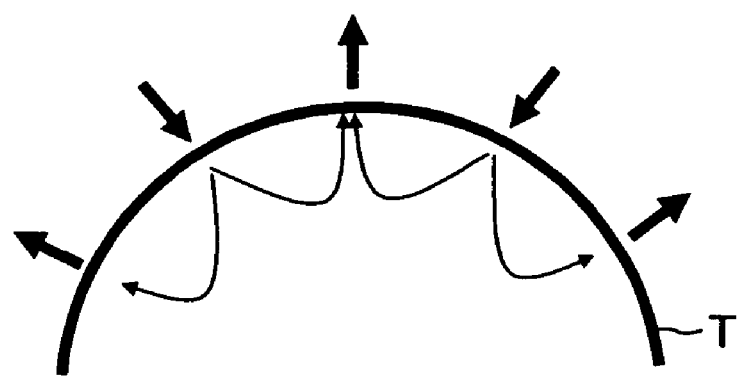
FIG. 6A is a schematic cross-sectional view showing the light scattering state in a head in the case of employment of a conventional biological information measuring apparatus.
Figure 6B:
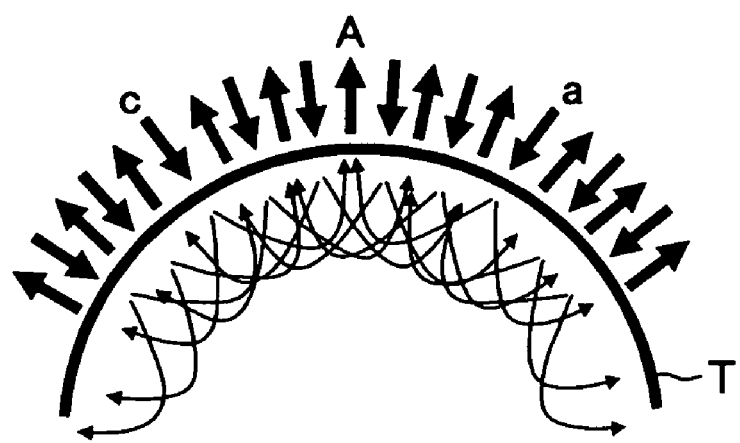
FIG. 6B is a schematic cross-sectional view showing the light scattering state in a head in the case of employment of the biological information measuring apparatus of FIG. 1.

In the biological information measuring apparatus S according to the present embodiment, one of the light detection sections 2 (e.g., the light detection section A) identifies a plurality of the light emission sections 1 (e.g., the light emission sections a to d), and selectively detects modulated light beams emitted from the thus-identified light emission sections 1. Therefore, measurement points can be densely arranged; i.e., the measurement resolution can be improved considerably. This improvement will next be described with reference to FIGS. 6A and 6B. FIGS. 6A and 6B schematically show the state where light beams (modulated light beams) injected into the head T through its surface are reflected at the cerebral cortical layer, and reach the surface of the head T. FIG. 6A shows the light scattering state in the case of a conventional biological information measuring apparatus, and FIG. 6B shows the light scattering state in the case of the biological information measuring apparatus S according to the present embodiment.

The conventional biological information measuring apparatus is also configured such that one light detection section receives light beams emitted from a plurality of light emission sections. However, the light detection section of the conventional biological information measuring apparatus does not identify the plurality of light emission sections for selective light beam reception. Therefore, in the conventional biological information measuring apparatus, the interval between the light detection section and the light emission sections is increased, whereby the number of reflected light beams received by the one light detection section is limited; i.e., the number of the light emission sections emitting light beams which can reach the one light detection section is limited. Therefore, as shown in FIG. 6A, the points of the cerebral cortical layer at which light beams injected into the head T are reflected are away from one another; i.e., the number of the measurement points is small, and thus the measurement resolution is poor.

In contrast, in the biological information measuring apparatus S according to the present embodiment, the light detection sections A to G employ PN sequences, and thus can identify the modulated light beams emitted from the light emission sections a to h on which the received reflected light beams are based. Therefore, even when the light emission sections 1 are densely arranged around the light detection sections 2, crosstalk does not occur, and, for example, the light detection section A can selectively detect only the reflected light beams of the modulated light beams emitted from the specific light emission sections a, b, c, and d. When the other light detection sections 2 (e.g., the light detection sections B to G) selectively detect only the reflected light beams of the modulated light beams emitted from the specific light emission sections 1 (e.g., the light emission sections e to h) in a manner similar to that described above, as shown in FIG. 6B, the points of the cerebral cortical layer at which modulated light beams injected into the head T are reflected are close to one another; i.e., the number of the measurement points is large. Therefore, the region targeted for measurement can be regarded as a measurement plane, and the measurement resolution is considerably improved. When, for example, the thus-obtained measurement results are graphically (e.g., two-dimensionally) displayed on the display section 4, change in blood flow associated with cerebral activity can be observed in detail. Since the light emission sections a to h and the light detection sections A to G can be densely arranged, the biological information measuring apparatus S can be downsized. In this measuring apparatus, when, for example, the light detection section A receives the reflected light beams of the modulated light beams emitted from the specific light emission sections a, b, c, and d, emission of modulated light beams from the light emission sections e, f, g, and h can be temporarily suppressed by means of the control section 3.

In the biological information measuring apparatus S according to the present embodiment, the control section 3 changes PN sequences output to the spread code sequence acquisition units 23, whereby the light detection sections 2 can selectively switch the light emission sections 1 to be identified. Thus, the blood oxygen level in the brain can be measured in a three-dimensional manner. In general, when a light beam is emitted from an emission point at a predetermined angle to a reflection object, the point which the reflected light beam reaches varies depending on the distance between the emission point and the reflection object. Specifically, in the case where a light beam is emitted from an emission point to a reflection object, when the distance between the emission point and the reflection object is small, the point which the reflected light beam reaches is close to the emission point, whereas when the distance between the emission point and the reflection object is large, the point which the reflected light beam reaches is away from the emission point. Even when modulated light beams are injected into the head T as described above, the above-described tendency generally occurs, although the paths of the reflected light beams cannot be strictly specified due to diffuse reflection of the modulated light beams in the head T.

Therefore, in the biological information measuring apparatus S according to the present embodiment, when the control section 3 causes the light detection section 2 to identify the light emission sections 1 such that the distance between the light detection section 2 and the light emission sections 1 equal to one of various distances, the blood oxygen level can be measured in a depth direction. This blood oxygen level measurement will next be specifically described with reference to FIGS. 4 and 7.

Figure 7A:
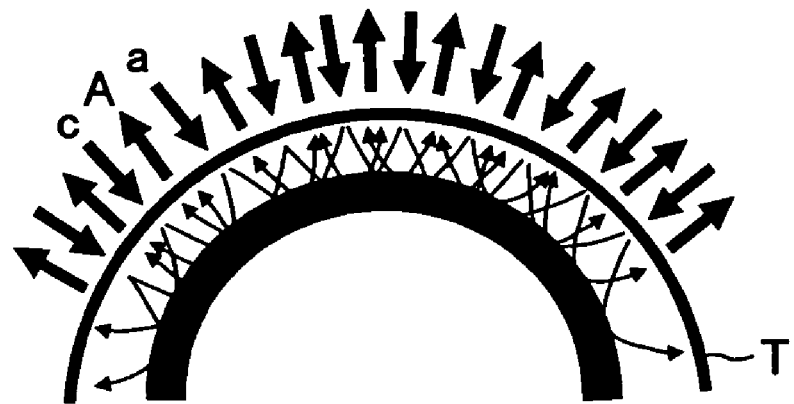
FIG. 7A is a schematic cross-sectional view showing the light reflecting state in a head in the case where the distance between a light emission point and a reflection object is small.

Now will be described the case where the blood oxygen level is measured at a somewhat superficial side of the cerebral cortical layer (e.g., the cerebral cortex). In this case, as schematically shown in FIG. 7A, the distance between the surface of the head T and the superficial side of the cerebral cortex is small. Therefore, for example, the control section 3 controls the light detection section A shown in FIG. 4 such that the section A receives the reflected light beams of the modulated light beams emitted from the light emission sections a to d, which are close to the section A. Specifically, the control section 3 acquires PN sequences generated from the spread code sequence generators 11 of the light emission sections a to d. Subsequently, the control section 3 supplies the thus-acquired PN sequences to the spread code sequence acquisition units 23 of the light detection section A. Thus, the light detection section A selectively detects the reflected light beams of the modulated light beams emitted from the light emission sections a to d, and outputs, to the control section 3, detection signals corresponding to the intensities of the thus-selectively-detected reflected light beams. Therefore, the blood oxygen level can be measured at the superficial side of the cerebral cortex.

Figure 7B:
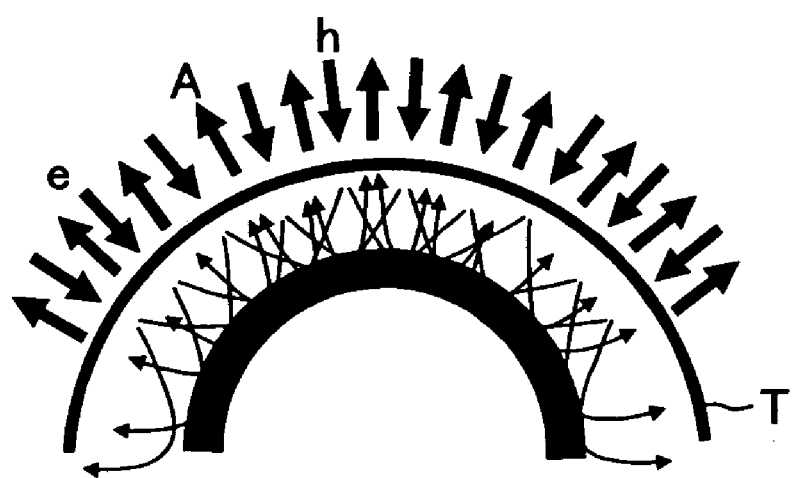
FIG. 7B is a schematic cross-sectional view showing the light reflecting state in a head in the case where the distance between a light emission point and a reflection object is large.

Next will be described the case where, for example, the blood oxygen level is measured at a somewhat back side of the cerebral cortex. In this case, as schematically shown in FIG. 7B, the distance between the surface of the head T and the back side of the cerebral cortex is large. Therefore, the control section 3 controls the light detection section A such that the section A receives the reflected light beams of the modulated light beams emitted from the light emission sections e to h, which are away from the section A as shown in FIG. 4. Specifically, the control section 3 acquires PN sequences generated from the spread code sequence generators 11 of the light emission sections e to h, and then supplies the thus-acquired PN sequences to the spread code sequence acquisition units 23 of the light detection section A. Thus, the light detection section A selectively detects the reflected light beams of the modulated light beams emitted from the light emission sections e to h, and outputs, to the control section 3, detection signals corresponding to the intensities of the thus-detected reflected light beams. Therefore, the blood oxygen level can be measured at the back side of the cerebral cortex. Meanwhile, in the case where the blood oxygen level is to be measured at a back side of the cerebral cortex, the emitted modulated light beams are significantly attenuated. Therefore, unlike the case where the blood oxygen level is measured at a superficial side of the cerebral cortex, the control section 3 outputs a driving signal for increasing the output intensities of the light sources 14 of the light emission sections e to h, or a driving signal for decreasing the output intensities of the light sources 14 of the light emission sections a to d. Alternatively, it is possible that the control section 3 does not output, to the light emission sections a to d, a driving signal for emitting modulated light beams.

The measurement results corresponding to different depth positions, which are obtained through the aforementioned three-dimensional measurement of the blood oxygen level in the brain, can be combined together through calculation. Thus, for example, the blood oxygen level in arteries or veins in the brain can be three-dimensionally displayed on a display of the display section 4, or change in blood flow associated with cerebral activity can be displayed in a three-dimensional manner. Therefore, cerebral activity can be noninvasively observed in detail.

In the biological information measuring apparatus S of the present embodiment, according to the driving signal output from the control section 3, the spread code sequence generators 11 of the light emission sections 1 generate PN sequences serving as spread code sequences, and output the thus-generated PN sequences to the control section 3. The control section 3 supplies the thus-output PN sequences to the spread code sequence acquisition units 23 of the light detection sections 2. Thus, the light detection sections 2 can despread the spread-spectrum-modulated signal corresponding to the modulated light beams emitted from the light emission sections 1.

Each of the PN sequences generated by the spread code sequence generators 11 can be regarded as a sequence of rectangular waves randomly taking the level "+1" or "−1." When the rate represented by the inverse number of the duration of each of the randomly occurring rectangular waves (hereinafter the rate will be referred to as a "chip frequency") is increased, the percent spreading of a driving signal (primary modulated signal) which is subjected to spread spectrum modulation by use of the PN sequences can be increased. In other words, when the chip frequency is increased, and the spread spectrum modulation is performed, the bandwidth of the modulated light beams emitted from the light emission sections 1 can be increased. Therefore, a rapid biological change in a living organism (e.g., nervous activity in a living organism) can also be measured as biological information.

Specifically, for example, when observation of a rapid biological change in a living organism is ordered by the operator via an unillustrated input apparatus, the control section 3 controls the light emission sections 1 such that chip frequency of the spread code sequence generators 11 of the sections 1 increases. When specific wavelengths are designated by the operator, as described above, the control section 3 supplies, to the light emission sections 1, a driving signal for emitting modulated light beams having the specific wavelengths. Thus, each of the light emission sections 1 subjects the driving signal (primary modulated signal) to spread spectrum modulation by use of PN sequences generated at high chip frequency by the spread code sequence generators 11, and the light sources 14 emit modulated light beams of large bandwidth on the basis of the thus-spread-spectrum-modulated signal (secondary modulated signal).

In general, conceivably, nervous activity in a living organism causes a slight change in the state of light scattering in the living organism. Therefore, when a plurality of the light emission sections 1 inject modulated light beams of large bandwidth into a living organism, and a plurality of the light detection sections 2 detect the intensities of the modulated light beams which have been emitted from specific light emission sections 1 and attenuated (i.e., reflected light beams), nervous activity in the living organism can be observed. In the biological information measuring apparatus S according to the present embodiment, since the chip frequency of the spread code sequence generators 11 is changed in accordance with the rate of change in biological information to be measured, the biological information can be measured in a very accurate and detailed manner. In addition, a rapid biological change occurring in a living organism can be real-time observed by displaying results of measurement of the change on the display section 4 almost simultaneous with this measurement.

The present invention is not limited to the above-described embodiment, and various modifications may be made without departing from the scope of the present invention.

For example, in the above-described embodiment, spread spectrum modulation of a driving signal (i.e., primary modulated signal) is performed by use of PN sequences generated by the spread code sequence generators 11. Specifically, in the above-described embodiment, the primary modulated signal is subjected to spread spectrum modulation by means of a direct spread system. However, spread spectrum modulation of the primary modulated signal may be performed by means of a frequency hopping system. In this case, the spread code sequence generators 11 of the light emission sections 1, which are employed in the above-described embodiment, are replaced by hopping synthesizers. Meanwhile, the spread code sequence acquisition units 23 of the light detection sections 2, which are employed in the above-described embodiment, are replaced by hopping synthesizers. For example, the control section 3 supplies the same hopping pattern to the hopping synthesizers of the light emission sections 1 and the light detection sections 2. When the control section 3 supplies predetermined different hopping patterns to the respective light emission sections 1, as in the case of the above-described embodiment, the light detection sections 2 can selectively identify specific light emission sections 1. Therefore, effects similar to those obtained in the above-described embodiment are envisaged to be attained.

In the above-described embodiment, one light emission section 1 is formed of a plurality of the light generation units 10. However, these individual light generation units 10 may be connected directly to the incident points. Thus, when a number of the light generation units 10 are provided, a number of modulated light beams having a plurality of specific wavelengths can be injected into a living organism, and therefore effects similar to those obtained in the above-described embodiment are envisaged to be attained.

In the above-described embodiment, the biological information measuring apparatus S is applied to the case where the blood oxygen level in the brain is measured. However, needless to say, the measuring apparatus can be applied to measurement of other types of biological information (e.g., biological density, water content, blood glucose level, lipid content, and pulse) by appropriately varying the specific wavelengths of light beams generated by a plurality of the light generation units 10 constituting the light emission sections 1. Thus, when the biological information measuring apparatus of the present invention is employed, biological information other than blood oxygen level can be measured in detail.

What is claimed is:

1. A biological information measuring apparatus comprising:

a plurality of light emission means, each adapted for modulating a predetermined primary modulated signal by spread spectrum modulation to thereby generate a secondary modulated signal, and for injecting a light beam into a living organism on the basis of the secondary modulated signal;

light detection means for receiving the light beams which have been emitted from the plurality of light emission means and transmitted through the living organism, for obtaining an electrical signal corresponding to the light beams through despreading, and for detecting a signal contained in the light beams on the basis of the electrical signal; and control means for controlling the operation of the light emission means and the light detection means, and for obtaining biological information associated with the metabolism of the living organism on the basis of the signal detected by the light detection means, wherein the control means comprises:

spread code sequence acquisition means for acquiring, from each respective light emission means of the plurality of light emission means, a different spread code sequence employed by the respective light emission means for spread spectrum modulation of the predetermined primary modulated signal; and spread code sequence supply means for supplying, to each of the light detection means, some, but not all of the different spread code sequences acquired by the spread code sequence acquisition means.

2. A biological information measuring apparatus according to claim 1, wherein the plurality of light emission means comprise a plurality of light generation means for respectively generating light beams having different specific wavelengths, and each of the light generation means comprises:

spread code sequence generation means for generating the spread code sequence;

spread spectrum modulation means for generating the secondary modulated signal through spread spectrum modulation of the predetermined primary modulated signal supplied from the control means by use of the above-generated spread code sequence; and light source driving means for driving a light source which emits a light beam having a specific wavelength on the basis of the secondary modulated signal generated by the spread spectrum modulation means.

3. A biological information measuring apparatus according to claim 2, wherein the spread code sequence generation means comprises periodic random number acquisition means for acquiring periodic random numbers supplied from the control means, and a frequency synthesizer for generating a random pattern regarding frequency in accordance with the above-acquired periodic random numbers.

4. A biological information measuring apparatus according to claim 2, wherein the spread code sequence generation means generates the spread code sequence by varying a chip frequency represented by the inverse number of the duration of occurrence of the spread code sequence.

5. A biological information measuring apparatus according to claim 2, wherein the light beams having different specific wavelengths which are respectively generated by the plurality of light generation means enter the living organism while being superposed on one another.

6. A biological information measuring apparatus according to claim 1, wherein the light detection means comprises:

light receiving means for receiving the light beams which have been transmitted through the living organism and generating an electrical signal corresponding to the received light beams;

spread code sequence acquisition means for acquiring a spread code sequence supplied from the control means;

despreading means for despreading the electrical signal by use of the thus-acquired spread code sequence, and for demodulating a signal contained in the light beams transmitted through the living organism; and output means for outputting the thus-demodulated signal to the control means.

7. A biological information measuring apparatus according to claim 1, wherein the light emission means and the light detection means are arranged in the form of a matrix.

8. A biological information measuring apparatus according to claim 1, wherein the light emission means and the light detection means are connected to the living organism via light conducting means.

9. A method implemented by a control means, the method for controlling a biological information measuring apparatus, and the method comprising:

acquiring, from each respective light emission means of a plurality of light emission means, a different spread code sequence employed by the respective light emission means for spread spectrum modulation of a primary modulated signal; and supplying, to each of a plurality of light detection means, some, but not all of the acquired different spread code sequences.

10. The method of claim 9, wherein the supplying comprises:

associating a particular light emission means and a particular light detection means by comparing (a) a distance between the particular light emission means and the particular light detection means to (b) a depth of measurement of biological information performed by the biological information measuring apparatus; and supplying a spread code sequence acquired from the particular light emission means to the particular light detection means.

11. The method of claim 9, further comprising:

varying, for a selected light emission means of the plurality of light emission means, a chip frequency represented by an inverse number of a duration of occurrence of the selected light emission means' spread code sequence.

* * * * *